United States Patent
Guenthenspberger et al.

(10) Patent No.: US 8,058,279 B2
(45) Date of Patent: Nov. 15, 2011

(54) INSECTICIDAL PYRIMIDINYL ARYL HYRDRAZONES

(75) Inventors: Katherine A. Guenthenspberger, Daleville, IN (US); Timothy C. Johnson, Indianapolis, IN (US); Noormohamed M. Niyaz, Indianapolis, IN (US); Ricky Hunter, Westfield, IN (US); Annette V. Brown, Indianapolis, IN (US); Tony K. Trullinger, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 485 days.

(21) Appl. No.: 12/238,998

(22) Filed: Sep. 26, 2008

(65) Prior Publication Data

US 2009/0093480 A1  Apr. 9, 2009

Related U.S. Application Data

(60) Provisional application No. 60/998,200, filed on Oct. 9, 2007.

(51) Int. Cl.
*A01N 43/54* (2006.01)
*C07D 239/48* (2006.01)
(52) U.S. Cl. ......... 514/256; 514/269; 514/275; 544/122
(58) Field of Classification Search .................. 514/256, 514/269, 275; 544/122
See application file for complete search history.

(56) References Cited

U.S. PATENT DOCUMENTS

| 6,660,733 | B2 | 12/2003 | Sun et al. |
| 6,693,097 | B2 | 2/2004 | Ono et al. |

FOREIGN PATENT DOCUMENTS

| WO | WO-2003030909 | 4/2003 |
| WO | WO-2003091223 | 11/2003 |
| WO | WO-2004006867 | 1/2004 |
| WO | PCT/US2008/077883 | 12/2008 |

*Primary Examiner* — Sharmila G Landau
*Assistant Examiner* — Kortney L Klinkel
(74) *Attorney, Agent, or Firm* — Carl D. Corvin; Craig E. Mixan

(57) ABSTRACT

Pyrimidinyl aryl hydrazones are effective at controlling insects.

14 Claims, No Drawings

INSECTICIDAL PYRIMIDINYL ARYL HYRDRAZONES

BACKGROUND OF THE INVENTION

This application claims the benefit of U.S. Provisional Application Ser. No. 60/998,200 filed on Oct. 9, 2007. The present invention concerns novel pyrimidinyl aryl hydrazones and their use in controlling insects, particularly lepidoptera and/or coleoptera. This invention also includes new synthetic procedures, intermediates for preparing the compounds, pesticide compositions containing the compounds, and methods of controlling insects using the compounds.

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

The present invention provides novel compounds with broad-spectrum activity against insects, particularly lepidoptera and/or coleoptera.

SUMMARY OF THE INVENTION

This invention concerns compounds useful for the control of insects, especially useful for the control of lepidoptera and/or coleoptera. More specifically, the invention concerns compounds of the formula (I)

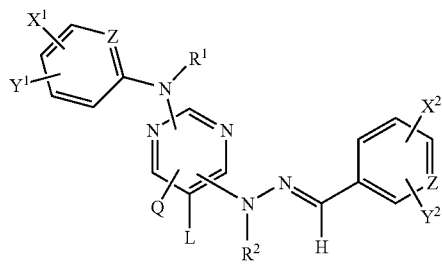

wherein $X^1$ and $Y^1$ independently represent H, halogen, $C_1$-$C_6$ haloalkyl, $C_1$-$C_6$ haloalkoxy, $C_1$-$C_6$ halothioalkyl, or $C_1$-$C_6$ haloalkyl substituted with hydroxy or $C_1$-$C_6$ acyloxy, with the proviso that at least one of $X^1$ or $Y^1$ is not H;

$X^2$ and $Y^2$ independently represent H, halogen, CN, $C_1$-$C_6$ alkoxy, $C_1$-$C_6$ haloalkyl, $C_1$-$C_6$ haloalkoxy, $C_1$-$C_6$ halothioalkyl, 1-pyrrolidinyl, 1-piperidinyl, or $C_1$-$C_6$ haloalkyl substituted with hydroxy or $C_1$-$C_6$ acyloxy, with the proviso that at least one of $X^2$ or $Y^2$ is not H;

Z represents CH or N;

L represents H, halogen or $C_1$-$C_3$-(halo)alkyl;

Q represents group H, halogen, $OR^3$, $C_1$-$C_3$-haloalkyl, $SR^3$ or $NR^4R^5$;

$R^1$ and $R^2$ independently represents H or $CH_3$;

$R^3$ represents $C_1$-$C_4$ alkyl which may be unsubstituted or substituted with from one to the maximum number of chloro or fluoro substituents;

$R^4$ represents H or $C_1$-$C_4$ alkyl;

$R^5$ represents: a) $C_1$-$C_4$ alkyl which may be unsubstituted or substituted with from one to the maximum number of chloro or fluoro substituents, or with a substituent selected from the group consisting of $C_1$-$C_4$ alkoxy, $C_1$-$C_4$ alkylamino and a pyridin-3-yl substituted in the 6-position of the pyridine ring with halogen, $C_1$-$C_4$ alkoxy or $C_1$-$C_4$ haloalkyl or b) $NR^4R^5$ taken together represent:

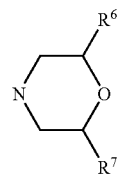

wherein $R^6$ and $R^7$ independently represent H or $CH_3$; or a phytologically acceptable acid addition salt thereof.

Preferred compounds of formula (I) include the following classes:

(A) Compound of formula (I) wherein Z is CH.

(B) Compounds of class (A) wherein one of $X^1$ and $Y^1$ is F, Cl, Br, CN, $CF_3$, $OCF_3$, $OCF_2CHF_2$ or $CH(CF_3)OH$.

(C) Compounds of class (B) wherein $X^1$ and $Y^1$ are meta- or para-substituents.

(D) Compounds of formula (I) wherein one of $X^2$ and $Y^2$ is F, Cl, Br, CN, $CF_3$, $OCF_3$, 1-pyrollidinyl, 1-piperidinyl, $OCF_2CHF_2$ or $C(CF_3)_2OH$.

(E) Compounds of class (D) wherein $X^2$ and $Y^2$ are meta- or para-substituents.

(F) Compounds of formula (I) wherein Q is H, Cl, F, $CF_3$, $CH_3OCH_2CH_2NH$, $EtNHCH_2CH_2NH$, $CF_3CH_2O$, morpholinyl or

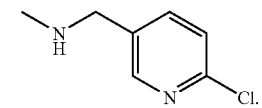

(G) Compounds of formula (I) wherein L is H, Cl, F or $CF_3$.

(H) Compounds of formula (I) having the structure

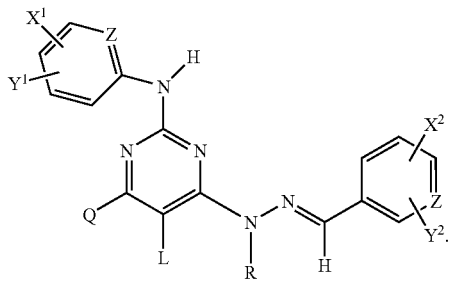

(I) Compounds of formula (I) having the structure

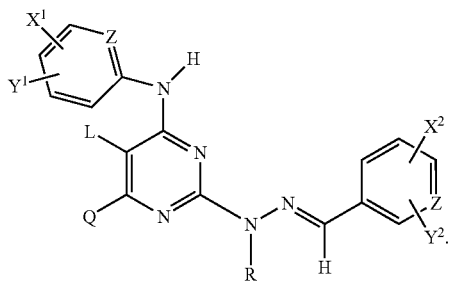

(J) Compounds of formula (I) having the structure

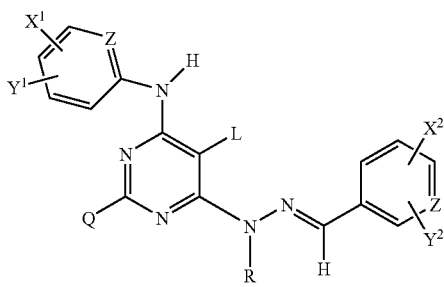

It will be appreciated by those skilled in the art that the most preferred compounds are generally those which are comprised of combinations of the above preferred classes.

The invention also provides new processes and intermediates for preparing compounds of formula (I) as well as new compositions and methods of use, which will be described in detail here-in-after.

DETAILED DESCRIPTION OF THE INVENTION

Throughout this document, all temperatures are given in degrees Celsius, and all percentages are weight percentages unless otherwise stated.

Unless specifically limited otherwise, the term "alkyl", as well as derivative terms such as "alkoxy", "thioalkyl" and "acyl", as used herein, include within their scope straight chain, branched chain, and cyclic moieties.

Unless specifically limited otherwise, the term "halogen", as well as derivative terms such as "halo", as used herein, refers to fluorine, chlorine, bromine, and iodine. Preferred halogens are fluorine and chlorine.

The term "haloalkyl" refers to alkyl groups substituted with from one up to the maximum possible number of halogen atoms. The terms "haloalkoxy" and "halothioalkyl" refer to alkoxy or thioalkyl groups substituted with from one up to the maximum possible number of halogen atoms.

The term "aryl", as used herein, refers to phenyl or pyridinyl.

Unless otherwise indicated, when it is stated that a group may be substituted with one or more substituents selected from an identified class, it is intended that the substituents may be independently selected from the class.

Synthesis of a compound of the formula (I) (where Z=CH) has been described in the literature ("Preparation of Pyrimidine Compounds as mixed Lymphocyte Reaction (MLR) inhibitors" Tsuruoka, Hiroyuki; Matsuda, Akihisa; Sugano, Yuichi; Tatsuta, Toru, WO2005037801).

Also, compounds of the formula (I) can be synthesized from commercially available 2,4,6-trihalopyrimidine (II) by stepwise addition of nucleophiles. More particularly, the compounds of the formula (I) can be synthesized according to the chemical processes outlined below.

General Method 1

In the first step, a 2,4,6-trihalopyrimidine of the formula (II) (where W=Cl or F; and L=H, F, Cl) is condensed with one equivalent of an aryl amine of the formula (III) in the presence of a base in a polar aprotic solvent to afford the mono aminated regioisomeric pyrimidine derivatives of the formula (IV) and (V) (Scheme 1). Other functional groups such as alkyl (or aryl) sulphonyl can be employed in place of W to effect this transformation. Trialkylamine such as diisopropylethylamine and inorganic bases such as potassium carbonate are the preferred bases for coupling, however, other organic or inorganic bases can be used. Although dioxane or tetrahydrofuran (THF) or dimethyl formamide (DMF) are used as the preferred solvents, other polar aprotic solvents can also be used to carry out this transformation.

Scheme 1

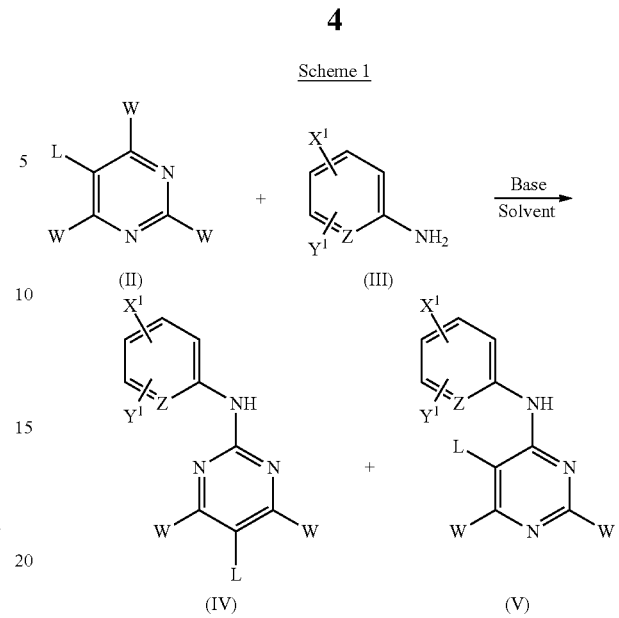

In the second step, the 2-arylamino pyrimidines of the formula (IV) (where W=Cl or F and L=H, F, Cl prepared according to Scheme 1) are reacted with excess hydrazine $RNHNH_2$ in an aprotic solvent to afford the compounds of the formula (VI) (Scheme 2). Although dioxane, THF or DMF are used as the preferred solvents, other polar aprotic solvents can be used to carry out this transformation.

Scheme 2

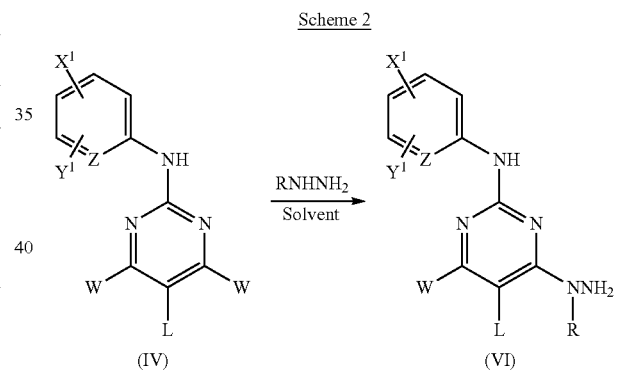

Similarly, 4-arylamino-2,6-dihaloropyrimidines of the formula (V) (where W=Cl or F; and L=H, F, Cl) are reacted with excess hydrazine $RNHNH_2$ in an aprotic solvent such as THF or dioxane or DMF to afford the compounds of the formula (VII) (Scheme 3). Although dioxane or THF or DMF are used as the preferred solvents, other polar aprotic solvents can also be used to carryout this transformation.

Scheme 3

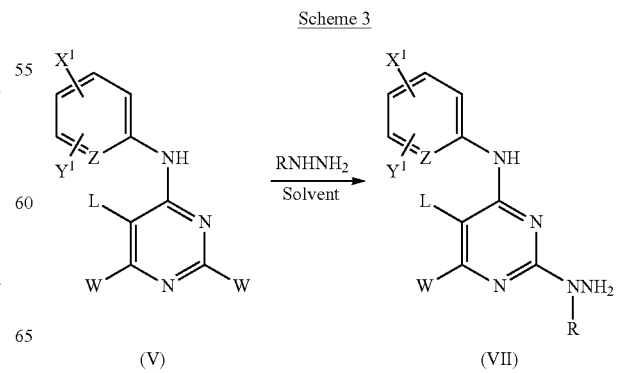

In the last step, the hydrazino derivative of the formula (VI) or (VII) are reacted with an aryl aldehyde of the formula (VIII) in a solvent such ethanol or a mixture of ethanol and another solvent such as THF or dichloromethane to give the compounds of the formula (I) (Scheme 4).

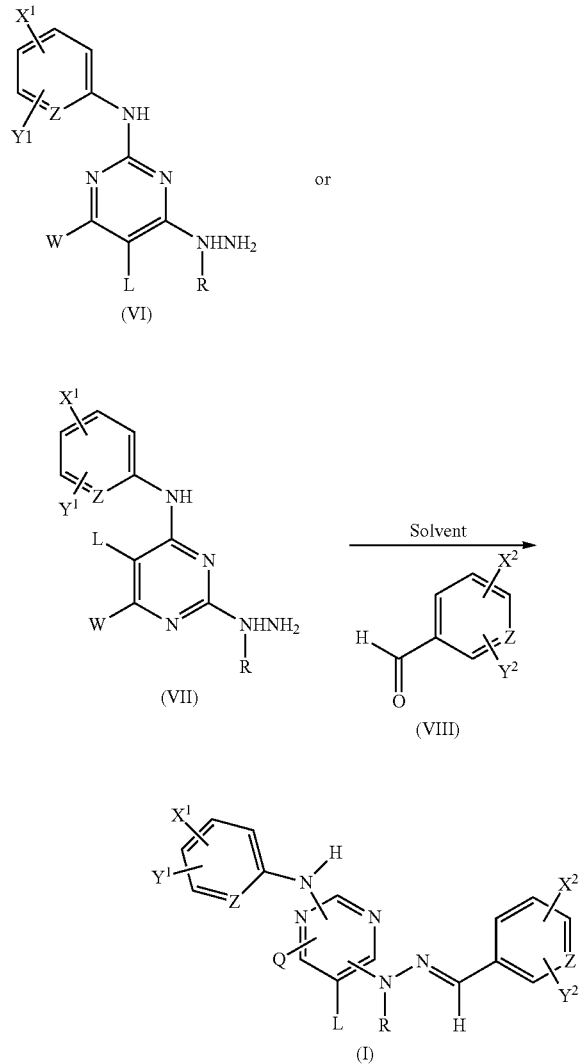

General Method 2

In Step 1 of this method, compounds of the formula (IV) (where W=Cl, F; L and R are as defined above) are reacted with an amine or (thio)alkoxy nucleophile (QH:) in the presence of a solvent to provide the compounds of the formula (IX) (Scheme 5). In Step 2, compounds of the formula (IX) are reacted with hydrazine of the formula RNHNH₂ in the presence of a base and a solvent to give the corresponding compounds of the formula (X) (Scheme 5). In step 3, compounds of the formula (X) are treated with aldehydes of the formula (VIII) to give the compounds of the formula (I). Ethanol, dioxane, THF and DMF are preferred solvents although other solvents can be used to carryout this transformation.

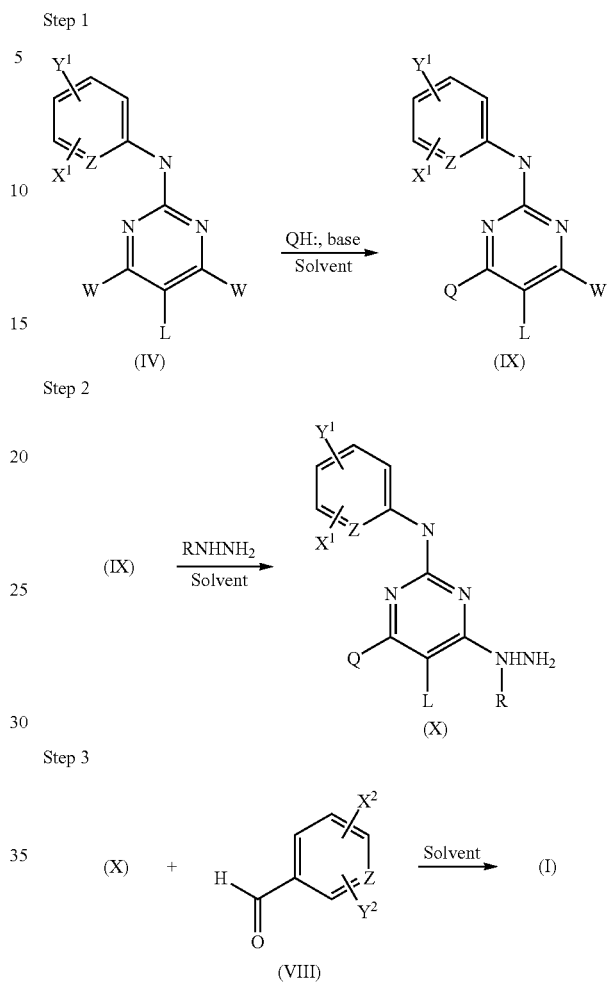

Similarly, compounds of the formula (V), prepared according to Scheme 1 (where W=Cl, F), are reacted with an amine or alkoxy nucleophile (QH) in the presence of a base and solvent to provide the regioisomeric compounds of the formula (XI) and (XII) (Scheme 6, Step-1). Compounds of the formula (XI) and (XII) are reacted with hydrazine RNHNH₂ in the presence of a solvent to give the corresponding compounds of the formula (XIII) and (XIV), respectively (Scheme 6, Step-2). In step 3, compounds of the formula (XIII) and (XIV) are treated with aldehydes of the formula (VIII) to give the compounds of the formula (I). Ethanol, dioxane, THF and DMF are preferred solvents although other solvents can be used to carry out these transformations.

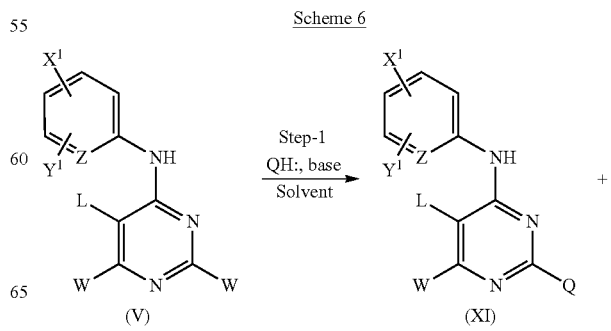

-continued

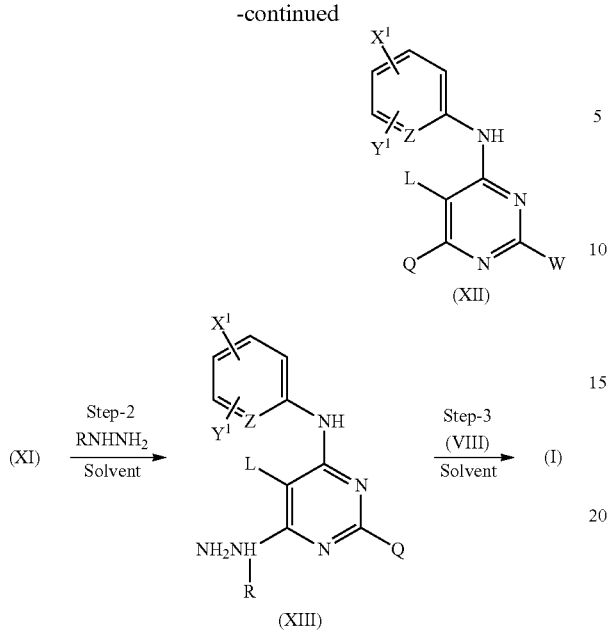

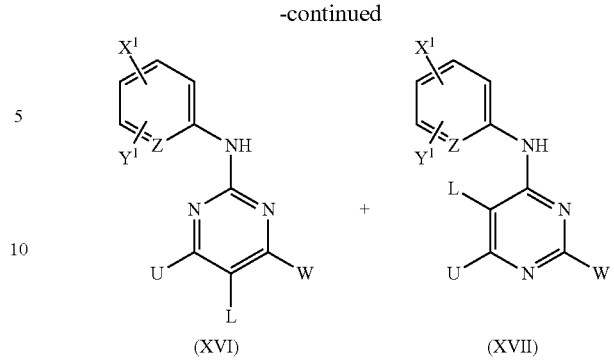

The arylamino pyrimidines of the formula (XVI) and (XVII) are reacted, individually, with hydrazine RNHNH$_2$ in the presence of a solvent to give the corresponding compounds of the formula (XVIII) and (XIX), respectively (Scheme 8). Compounds of the formula (XVIII) and (XIX) are treated, individually, with aldehydes of the formula (VIII) in a solvent to give the compounds of the formula (I) (Scheme 8). Ethanol, dioxane, THF and DMF are preferred solvents although other solvents can be used to carry out these transformations.

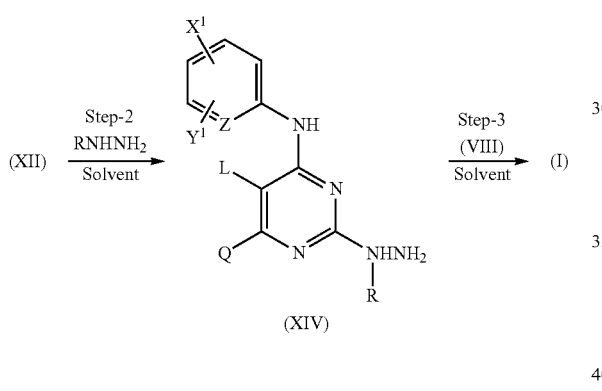

General Method 3

In this method a halopyrimidine intermediate of the formula (XV) [where U=(halo)alkyl and W=H, Cl, F, S(O)$_n$R$_2$ (n=0-2)] is condensed with one equivalent of an aryl amine of the formula (III) in the presence of a base in a polar aprotic solvent to afford the mono aminated regioisomeric pyrimidine derivatives of the formula (XVI) and (XVII) (Scheme 7). Trialkylamines such as diisopropyl-ethylamine and inorganic bases such as potassium carbonate are the preferred bases for this coupling, however, other organic or inorganic bases can be used. Although dioxane or THF or DMF are used as the preferred solvents, other polar aprotic solvents can also be used to carryout this transformation.

Scheme 8

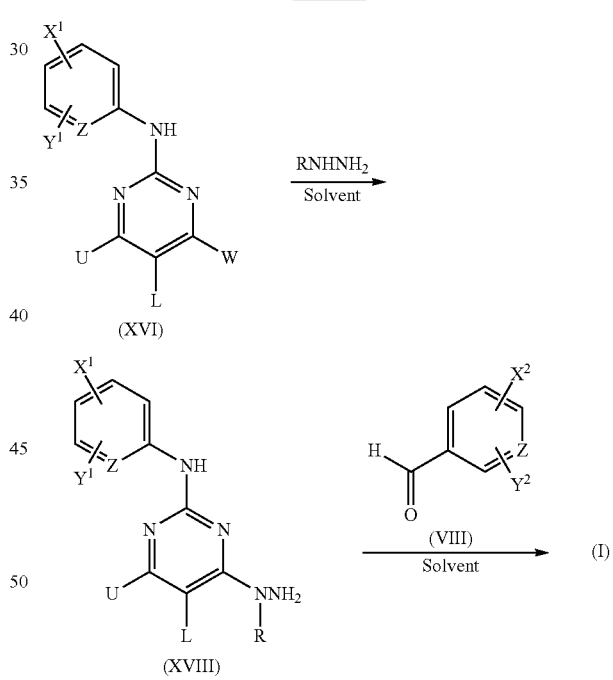

Scheme 7

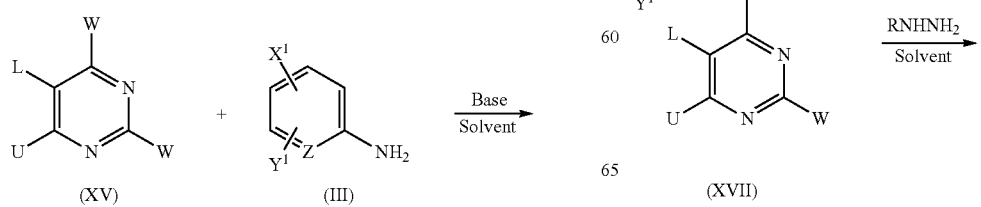

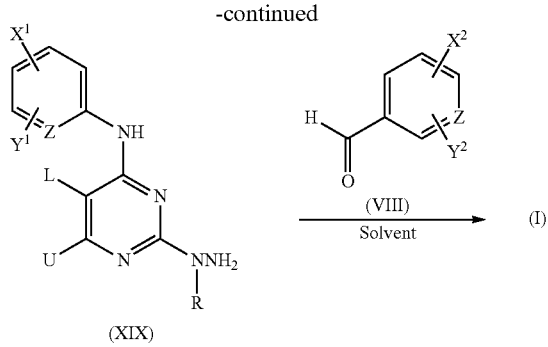

EXAMPLES

Example 1

(6-Chloro-2-{N'-[1-(4-trifluoromethoxyphenyl)-methylidene]-hydrazino}-pyrimidin-4-yl)-(4-fluoro-3-trifluoromethylphenyl)amine (1)

Compound 1 was prepared in three steps according to the Scheme 9.

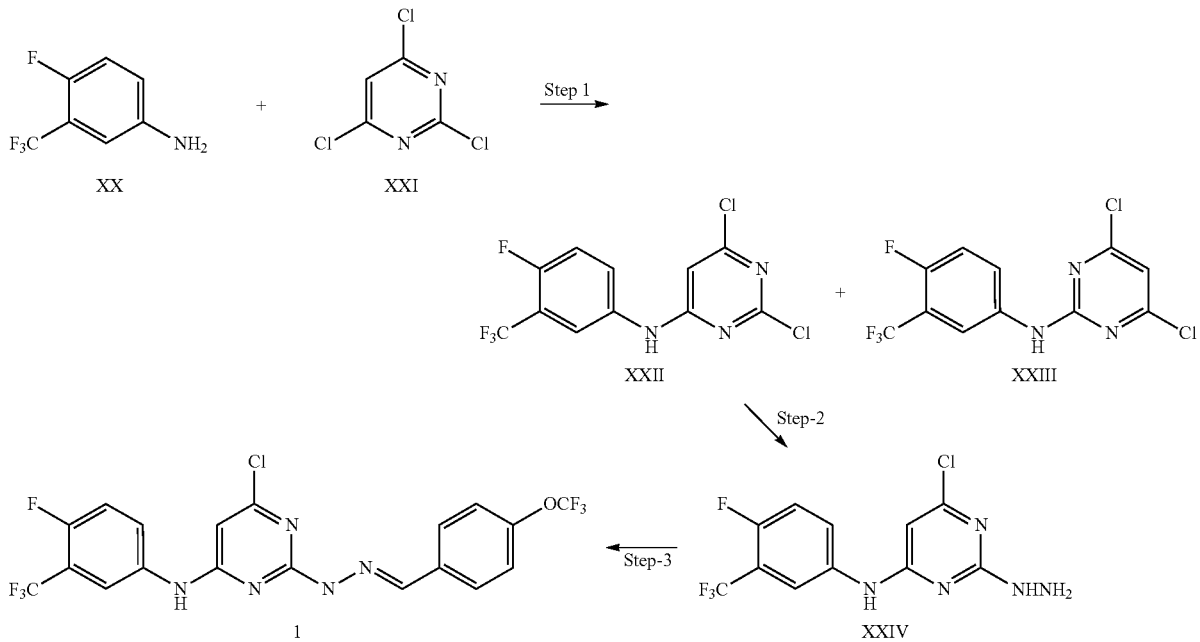

Scheme 9

Conditions
Step-1. Dioxane, i-Pr₂(Et)N, 80° C.;
Step-2. Hydrazine, THF;
Step-3. EtOH, 4-trifluoromethoxybenzaldehyde (2,6-Dichloro-pyrimidin-4-yl)-(4-fluoro-3-trifluoromethylphenyl)amine (XXII)

To a stirred solution of commercially available 2,4,6-trichloropyrimidine (XXI) (10.0 g, 52.5 mmol) and diisopropylethylamine (7.7 g, 52.5 mmol) in dioxane (50 mL) under inert atmosphere was added a solution of 4-fluoro-3-trifluoromethylaniline (XX) (9.70 g, 52.5 mmol) in dioxane (150 mL) and then the mixture was heated to 80° C. and stirred for 12 h. The mixture was cooled to ambient temperature and diluted with ether (200 mL) and water (50 mL). The organic phase was separated, successively rinsed with 1N aqueous hydrochloric acid and saturated brine, dried over anhydrous sodium sulfate and filtered. Removal of the volatiles under vacuum on a rotary evaporator gave a gummy solid. This solid was purified by flash column chromatography (silica gel, hexanes/ethyl acetate) to give two isomeric products (2,6-dichloropyrimidin-4-yl)-(4-fluoro-3-trifluoromethylphenyl)amine (XXII) (11.2 g, 63% yield) and (4,6-dichloropyrimidin-2-yl)-(4-fluoro-3-trifluoromethylphenyl)amine (XXIII) (5.2 g 29% yield). Compound XXII: m.p. 129-130° C.; $^1$H NMR (CDCl$_3$) δ 7.60 (m, 2H), 7.28 (m, 1H), 6.45 (s, 1H); GCMS (m/z) 325 (M−1$^+$); Compound XXIII: m.p.=102-104° C.; $^1$H NMR (CDCl$_3$) δ 7.86 (dd, J=6.6, 2.7 Hz, 1H), 7.76 (m, 1H), 7.20 (t, J=6.6 Hz, 1H), 6.84 (s, 1H); GCMS (m/z) 325 (M−1$^+$)

(2-Chloro-6-hydrazinopfrimidin-4-yl)-(4-fluoro-3-trifluoromethylphenyl)amine (XXIV)

To a stirred solution of (2,6-dichloropyrimidin-4-yl)-(4-fluoro-3-trifluoro-methylphenyl)amine (XXII) (2.5 g, 7.66 mmol) in dioxane (15 mL) was added hydrazine monohydrate (1 mL) and the mixture stirred at ambient temperature for 24 h. The mixture was diluted with water and the resulting slurry was stirred for 10 min then filtered under vacuum. The white precipitate was rinsed with water and dried under vacuum to give (2-chloro-6-hydrazinopyrimidin-4-yl)-(4-fluoro-3-trifluoromethylphenyl)amine (XXIV) as a white solid (2.1 g, 85% yield): m.p. 102-103° C., $^1$H NMR (CDCl$_3$) δ 7.7 (m. 1H), 7.59 (m, 1H), 7.21 (m, 1H), 5.95 (s, 1H), 3.77 (s, 3H); ESI/MS 325 (M−H).

(6-Chloro-2-{N'-[1-(4-trifluoromethoxyphenyl)-methylidene]hydrazino}-pyrimidin-4-yl)-(4-fluoro-3-trifluoromethylphenyl)amine (1)

To a stirred solution of hydrazine XXIV (321 mg, 1 mmol) in ethanol (1 mL) was added the 4-trifluoromethoxybenzaldehyde (285 g, 1.5 mmol) and the mixture stirred at ambient temperature for 2 h. The reaction mixture was concentrated and the residue was recrystallized from a mixture hot hexane-ether to give compound 1 as a white solid (357 mg, 72%): m.p. 162-164° C.; $^1$H NMR (DMSO-d$_6$) δ 10.70 (bs, 1H), 9.34 (bs, 1H), 8.07 (bs, 1H), 7.95 (s, 1H), 7.86 (m, 1H), 7.65 (d, J=8.7 Hz, 2H), 7.39 (s, 1H), 7.10 (d, J=8.7 Hz), 6.10 (s, 1H); ESI/MS 494 (M+H).

Example 2

Methyl-(4-trifluoromethoxyphenyl)-(2-{N'-[1-(4-trifluoromethoxy-phenyl)-methylidene]-hydrazino}-6-trifluoromethylpyrimidin-4-yl)amine (2)

Synthesis of compound 2 is illustrated in Scheme 10.

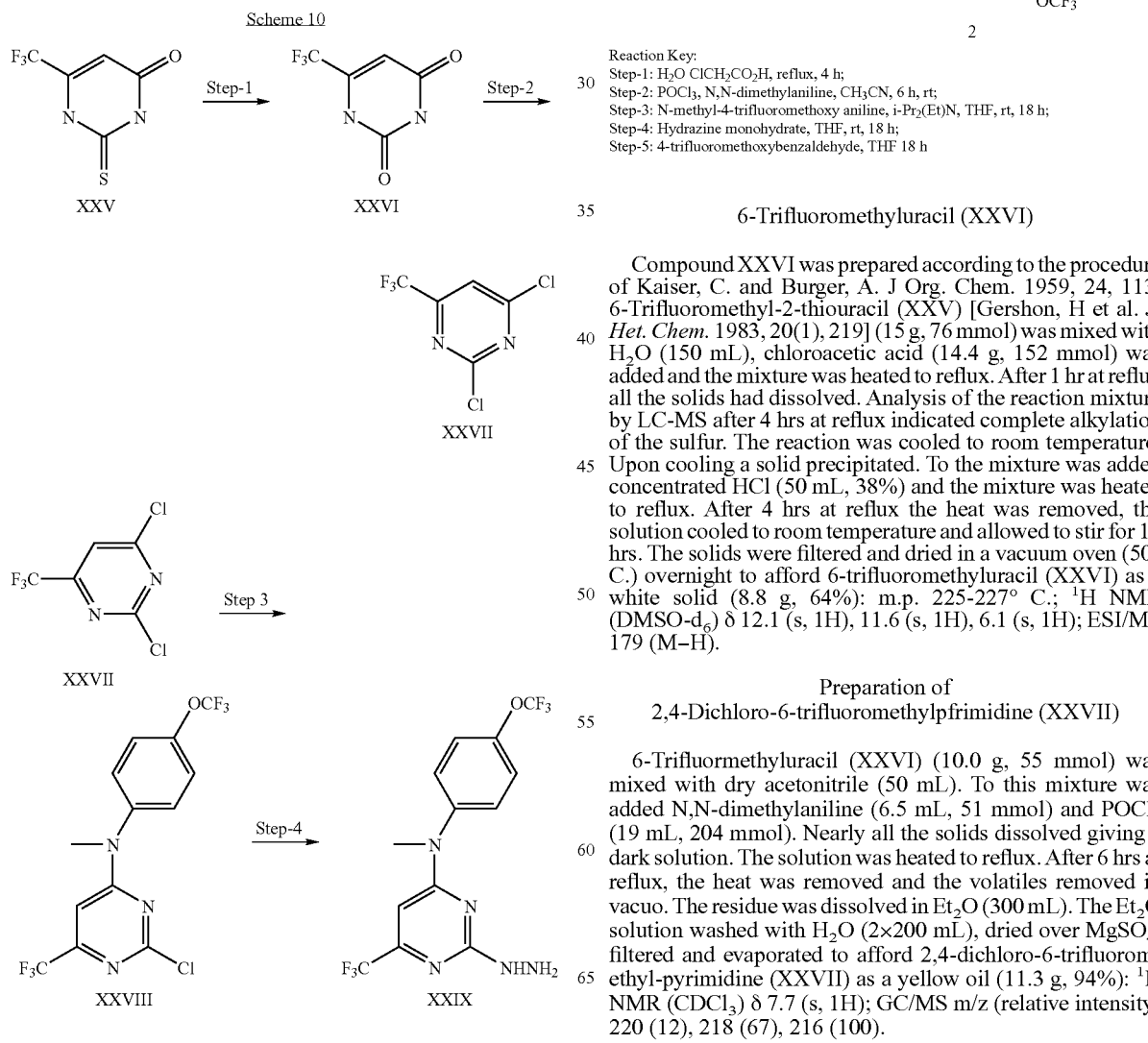

Reaction Key:
Step-1: H$_2$O ClCH$_2$CO$_2$H, reflux, 4 h;
Step-2: POCl$_3$, N,N-dimethylaniline, CH$_3$CN, 6 h, rt;
Step-3: N-methyl-4-trifluoromethoxy aniline, i-Pr$_2$(Et)N, THF, rt, 18 h;
Step-4: Hydrazine monohydrate, THF, rt, 18 h;
Step-5: 4-trifluoromethoxybenzaldehyde, THF 18 h 6-Trifluoromethyluracil (XXVI)

Compound XXVI was prepared according to the procedure of Kaiser, C. and Burger, A. J Org. Chem. 1959, 24, 113. 6-Trifluoromethyl-2-thiouracil (XXV) [Gershon, H et al. *J. Het. Chem.* 1983, 20(1), 219] (15 g, 76 mmol) was mixed with H$_2$O (150 mL), chloroacetic acid (14.4 g, 152 mmol) was added and the mixture was heated to reflux. After 1 hr at reflux all the solids had dissolved. Analysis of the reaction mixture by LC-MS after 4 hrs at reflux indicated complete alkylation of the sulfur. The reaction was cooled to room temperature. Upon cooling a solid precipitated. To the mixture was added concentrated HCl (50 mL, 38%) and the mixture was heated to reflux. After 4 hrs at reflux the heat was removed, the solution cooled to room temperature and allowed to stir for 18 hrs. The solids were filtered and dried in a vacuum oven (50° C.) overnight to afford 6-trifluoromethyluracil (XXVI) as a white solid (8.8 g, 64%): m.p. 225-227° C.; $^1$H NMR (DMSO-d$_6$) δ 12.1 (s, 1H), 11.6 (s, 1H), 6.1 (s, 1H); ESI/MS 179 (M−H).

Preparation of 2,4-Dichloro-6-trifluoromethylpfrimidine (XXVII)

6-Trifluormethyluracil (XXVI) (10.0 g, 55 mmol) was mixed with dry acetonitrile (50 mL). To this mixture was added N,N-dimethylaniline (6.5 mL, 51 mmol) and POCl$_3$ (19 mL, 204 mmol). Nearly all the solids dissolved giving a dark solution. The solution was heated to reflux. After 6 hrs at reflux, the heat was removed and the volatiles removed in vacuo. The residue was dissolved in Et$_2$O (300 mL). The Et$_2$O solution washed with H$_2$O (2×200 mL), dried over MgSO$_4$, filtered and evaporated to afford 2,4-dichloro-6-trifluoromethyl-pyrimidine (XXVII) as a yellow oil (11.3 g, 94%): $^1$H NMR (CDCl$_3$) δ 7.7 (s, 1H); GC/MS m/z (relative intensity) 220 (12), 218 (67), 216 (100).

(2-Chloro-6-trifluoromethylpyrimidin-4-yl)-methyl-(4-trifluoromethoxyphenyl)-amine (XXVIII)

2,4-Dichloro-6-trifluoromethylpyrimidine (XXVII) (1.00 g, 4.6 mmol) was dissolved in dry THF (5 mL). To this solution was added N-methyl-4-trifluoromethoxyaniline (0.88 g, 4.6 mmol) and diisopropylethylamine (0.8 mL, 4.6 mmol). The resulting solution was stirred at room temperature for 18 hrs, then the volatiles were removed in vacuo and the residue was dissolved in $CH_2Cl_2$ (50 mL). The $CH_2Cl_2$ solution was washed with 2N HCl, dried over $MgSO_4$, filtered and then concentrated in vacuo to give a brown color oil. Purification of the brown oil by chromatography (silica, hexane/EtOAc) afforded the product (XXVIII) as a yellow solid (0.95 g, 56%): $^1$H NMR ($CDCl_3$) δ 7.42-7.27 (m, 4H), 6.4 (s, 1H), 3.5 (s, 3H); GC/MS m/z (relative intensity) 374 (26), 373 (45), 372 (76), 370 (100).

(2-Hydrazino-6-trifluoromethylpyrimidin-4-yl)-methyl-(4-trifluoromethoxy-phenyl)amine (XIX)

To a solution of XXVIII (475 mg, 1.28 mmol) in dry THF (3 mL) was added methylhydrazine (273 μL, 5.13 mmol). The resulting solution was stirred at room temperature for 18 hrs, the solvent removed in vacuo and the residue taken up in $CH_2Cl_2$. The $CH_2Cl_2$ solution was washed with $H_2O$, dried over $MgSO_4$, filtered and $CH_2Cl_2$ evaporated in vacuo to afford XIX as a yellow oil (0.43 g, 88%): $^1$H NMR (DMSO-$d_6$) δ 7.48 (app s, 2H), 7.47 (app s, 2H), 5.84 (s, 1H), 4.86 (bs, 2H), 3.42 (s, 3H), 3.19 (s, 3H); ESIUMS 381 (M+H), 366 (M−$CH_3$).

Methyl-(4-trifluoromethoxyphenyl)-(2-{N'-[1-(4-trifluoromethoxyphenyl)-methylidene]-hydrazino}-6-trifluoromethylpyrimidin-4-yl)amine (2)

To a solution of 4-trifluoromethoxybenzaldehyde (117 μL, 1.2 mmol) in dry THF (3 mL) was added XXIX (0.37 g, 1.0 mmol). The solution is stirred 18 hrs and then the THF evaporated in vacuo. Purification of the residue by chromatography (silica gel, hexanes/EtOAc) afforded 2 as a white solid (0.50 g, 92%): m.p. 180-182° C.; $^1$H NMR (DMSO-$d_6$) δ 11.5 (bs, 1H), 7.73 (d, J=8.9, 2H), 7.53 (d, J=9.2, 2H), 7.50 (d, J=8.9, 2H), 7.38 (d, J=8.6, 2H) 6.14 (bs, 1H), 3.49 (s, 3H); ESI/MS 540 (M+H), 538 (M−H).

Example 3

N-[2-(6-Chloropyridin-3-ylmethyl)]-N-[4-(4-fluoro-3-trifluoromethylphenyl)]-6-{N'-[1-(4-trifluoromethoxyphenyl)-methylidene]-hydrazino}pyrimidine-2,4-diamine (3)

Preparation of 3 is outlined in Scheme 11.

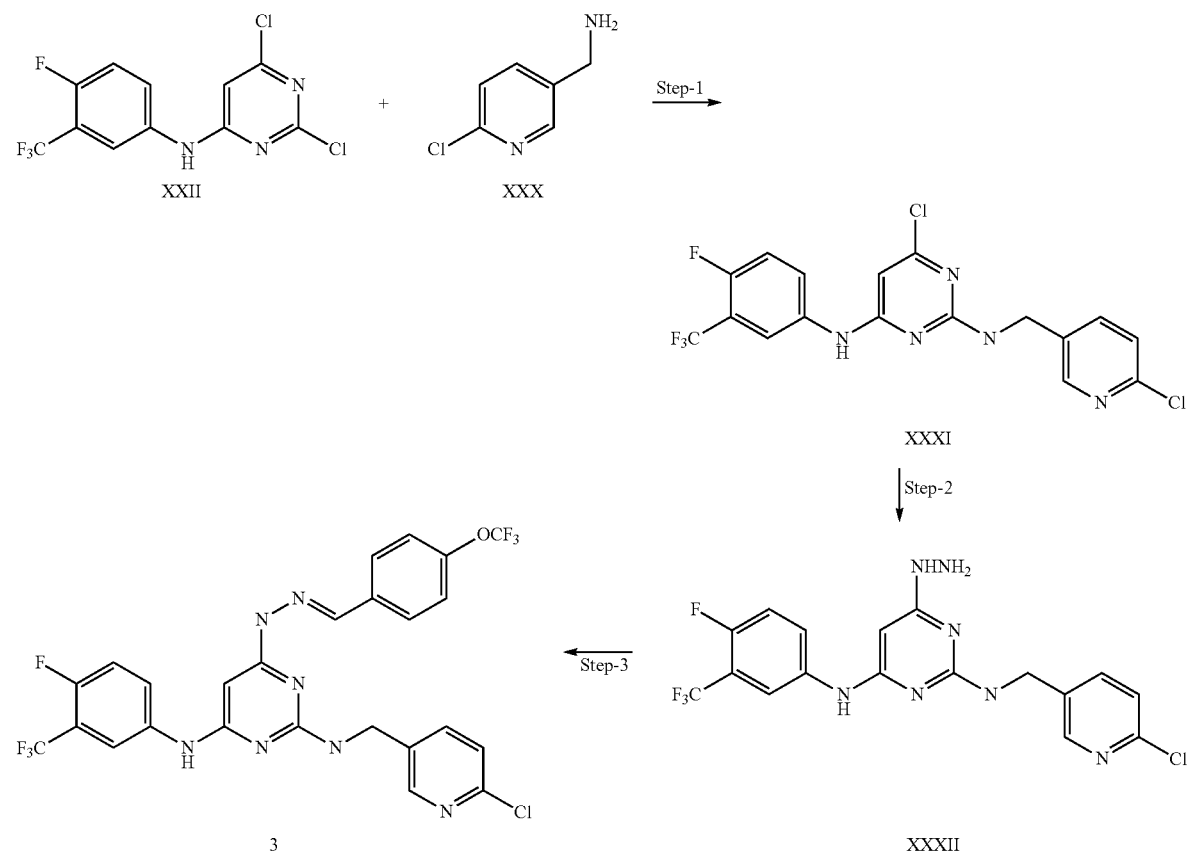

Conditions
Step-1. Dioxane, i-Pr2(Et)N, 50° C.;
Step-2. Hydrazine, THF, 80° C.;
Step-3. EtOH, 4-trifluoromethoxybenzaldehyde To a stirred solution of (2,6-dichloropyrimidin-4-yl)(4-fluoro-3-trifluoromethylphenyl)amine (XXII) (3.26 g, 10 mmol) in dioxane (15 mL) were added diisopropylethylamine (1.55 g, 10 mmol) and ((6-chloropyridin-3-yl)methyl)amine (XXX) (1.43 g, 10 mmol) and the mixture was stirred at 50° C. for 16 h. The mixture was diluted with water and stirred vigorously for 10 min. The white slurry was filtered to give a precipitate which was washed with water and dried under vacuum to give XXXI as a white solid (2.95 g, 68% yield). To a solution of this solid (432 mg, 1 mmol) in dioxane (1 mL) was added hydrazine monohydrate (0.5 mL) and the mixture stirred at 80° C. for 36 h. The reaction mixture was cooled to ambient temperature, diluted with water (15 mL), and stirred vigorously for 30 min resulting in a white precipitate. This precipitate was filtered and washed with water, and dried under vacuum to give 0.40 g (88% yield) of XXXII (m.p. 127-129° C.). To a solution of crude compound XXXII (214 mg, 0.5 mmol) in ethanol (2 mL) was added 4-trifluoromethoxy benzaldehyde (140 mg, 0.75 mmol) and the mixture stirred for 30 min at ambient temperature. The mixture was concentrated in vacuo and the residue was purified by column chromatography (silica gel, hexanes/ethyl acetate) to give 3 as a white solid (122 mg, 40% yield): $^1$H NMR (CDCl$_3$) δ 8.38 (s, 1H), 7.81 M, 1H), 7.70 (s, 1H), 7.63 (m, 3H), 7.43 (m, 1H), 7.20 (m, 4H), 6.04 (s, 1H), 4.56 (d, J=5.7 Hz, 2H); ESIUMS 600.13 (M+H).

Insecticidal Testing

The compounds identified in Table 1 were prepared using the procedures illustrated in the foregoing examples, and the compounds were tested against beet armyworm and corn earworm as follows:

Insecticidal Test for Corn Earworm (*Helicoverpa zea*) and Beet Armyworm (*Spodoptera exoua*).

To prepare test solution, the test compound was formulated at 2000 ppm solution as 4 mg/2 mL of 9 acetone:1 tap water. 50 μL of the 2000 ppm (equivalent to 50 ug/cm$^2$ dose on diet surface area) test solution was pipetted upon the surface of 1 mL of lepidopteran diet (Southland Multi-Species Lepidopteran Diet) contained in each of eight wells per insect species (one well=1 replication).

A second-instar corn earworm and beet armyworm was placed upon the treated diet in each well once the solvent had air-dried. Trays containing the treated diet and larvae were covered and then held in a growth chamber at 25° C., 50-55% RH, and 16 hr light:8 hr dark for 5 days. Observation were conducted 5 days after treatment and infestation. The number of dead insects of 8 per species per treatment was then determined and the results are given in Table 1 as percent control at a dose of 50 mg/cm$^2$.

Keys to the table: Mass spectral data were obtained using liquid chromatography mass spectroscopy (LC-MS). The masses are detected using electrospray ionization (ESI) and reported as Mol Ion (M+H, M−H); AVG LAPHEG 50 refers to activity against beet army worm (*Spodoptera exigua*) as defined above; AVG HELIZE 50 refers to activity against corn ear worm (*Helicoverpa zea*) as described above.

TABLE 1

| Cpd # | Structure | HELIZE 50 (ug/cm2) | LAPHEG 50 (ug/cm2) | Phy. App. | mp (° C.) |
|---|---|---|---|---|---|
| 1 | 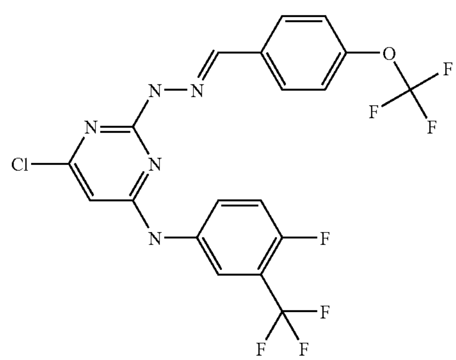 | 100 | 100 | white solid | 162-164 |
| 2 | 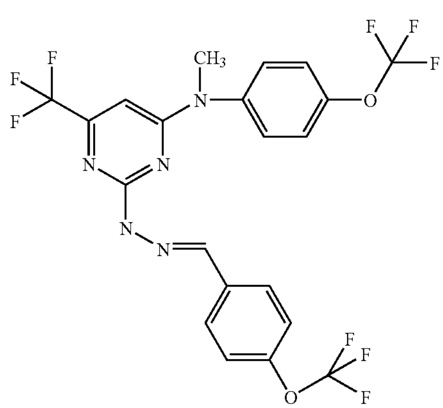 | 50 | 0 | white solid | 180-182 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 3 | 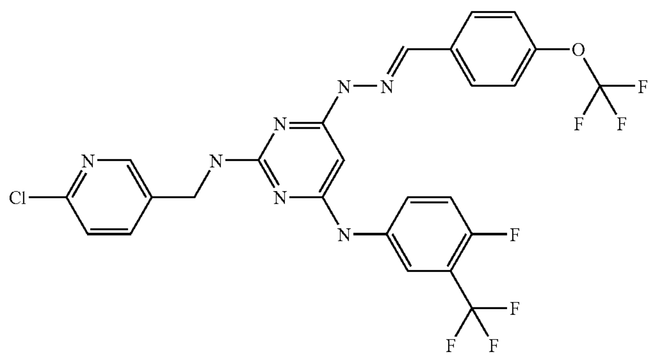 | 100 | 100 | white solid | 130-132 |
| 4 | 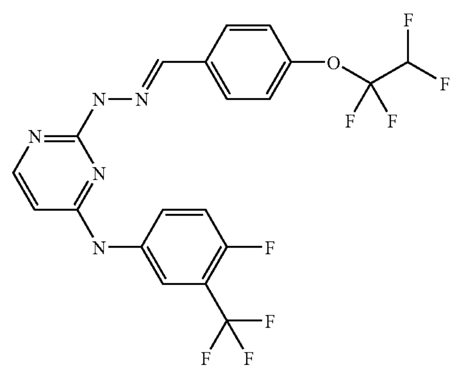 | 100 | 100 | off white solid | n/a |
| 5 | 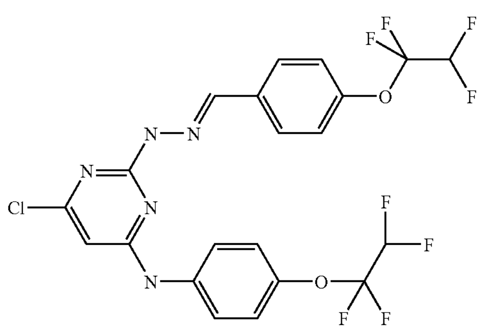 | 88 | 100 | white solid | 134-135 |
| 6 | 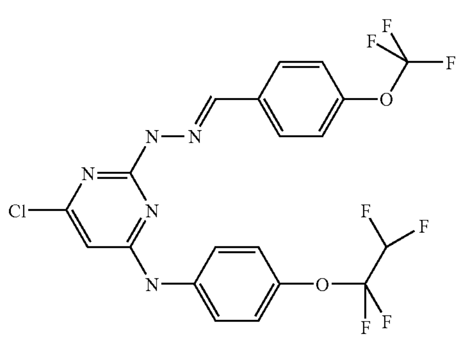 | 100 | 100 | white solid | 143-145 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 7 | 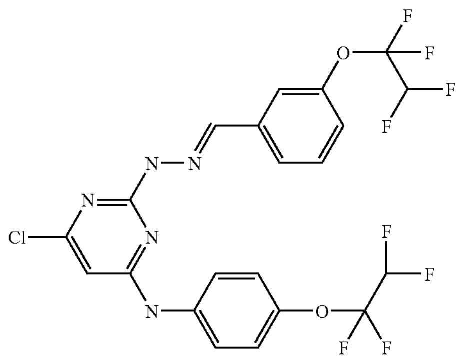 | 25 | 88 | white solid | 129-130 |
| 8 | 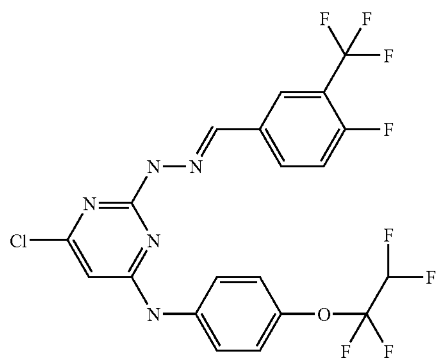 | 100 | 100 | white solid | 155-155.5 |
| 9 | 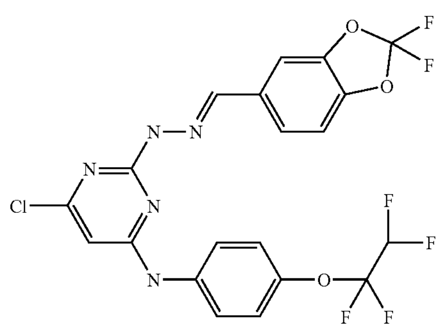 | 100 | 100 | white solid | 153-154 |
| 10 | 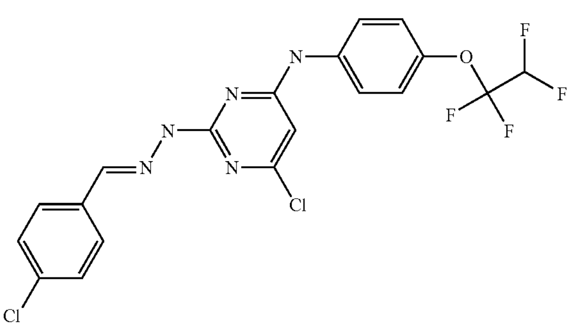 | 88 | 63 | white solid | 167-168 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 11 | 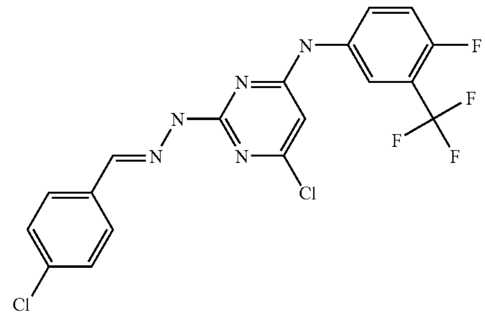 | 100 | 100 | white solid | 185-186 |
| 12 | 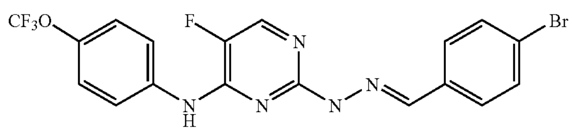 | 100 | 0 | yellow solid | 218-220 |
| 13 | 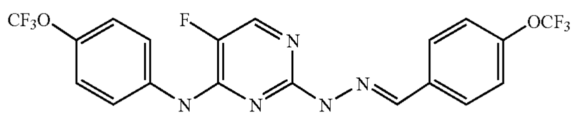 | 100 | 0 | yellow solid | 202-204 |
| 14 | 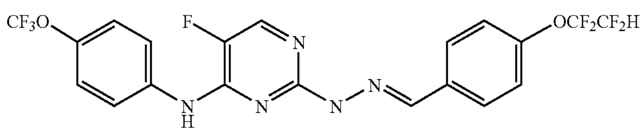 | 88 | 0 | light tan solid | 223-225 |
| 15 | 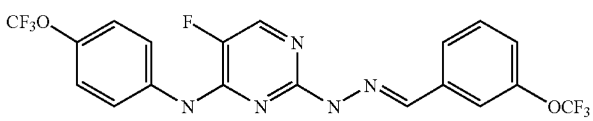 | 75 | 0 | yellow solid | 161-163 |
| 16 | 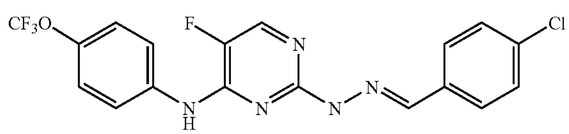 | 100 | 100 | yellow solid | 208-210 |
| 17 | 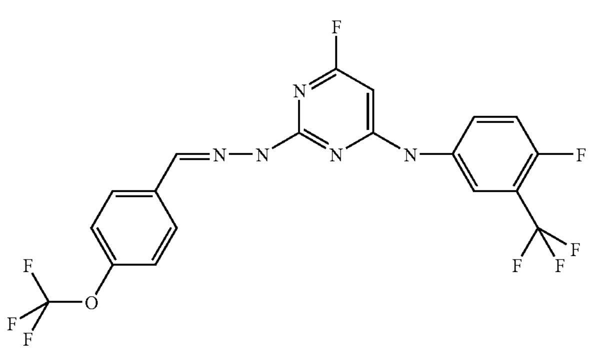 | 100 | 100 | white solid | 159-160 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 18 | 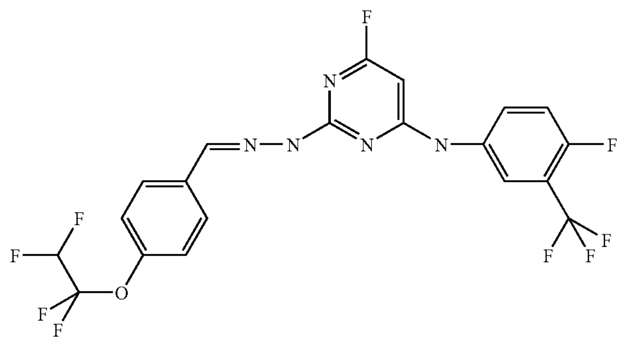 | 100 | 100 | white solid | 138-140 |
| 19 | 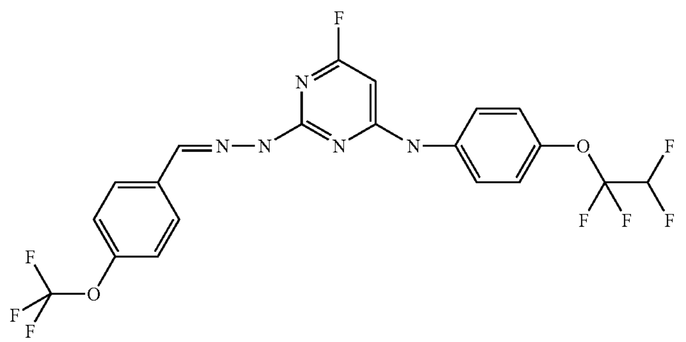 | 13 | 50 | white solid | 210-211 |
| 20 | 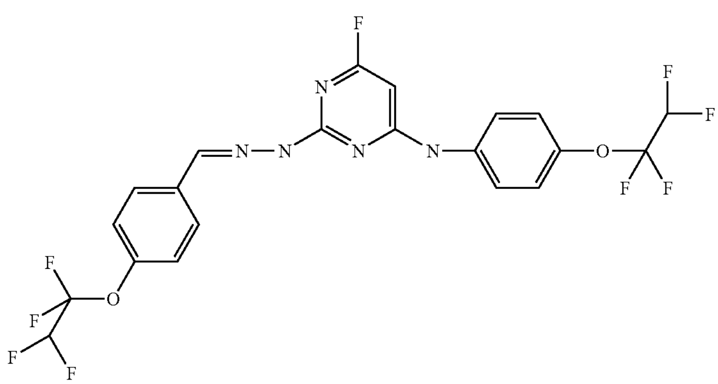 | 25 | 50 | white solid | 196-198 |
| 21 | 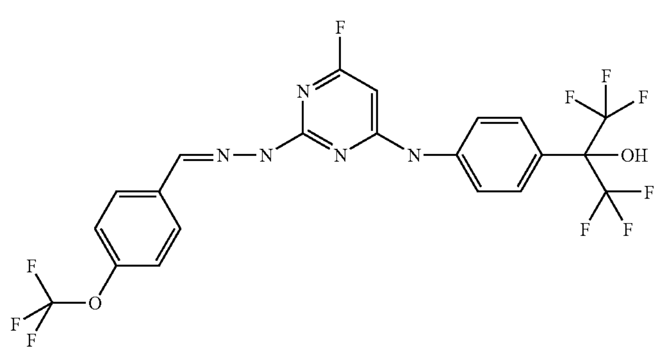 | 100 | 100 | white solid | 138-140 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 22 | 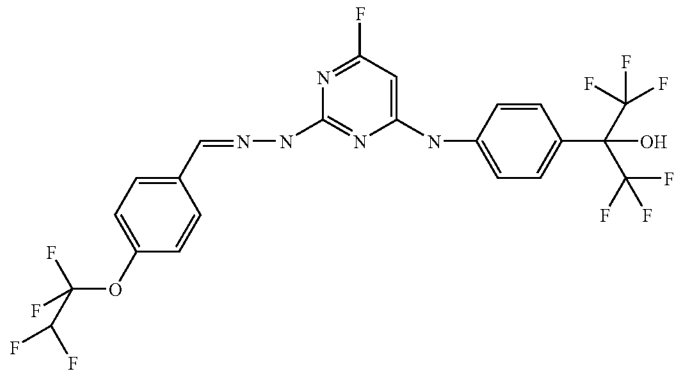 | 100 | 100 | white solid | 210-211 |
| 23 | 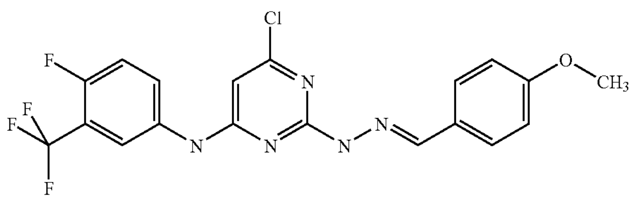 | 38 | 50 | White solid | 195-196 |
| 24 | 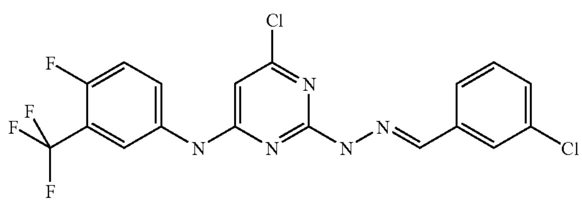 | 100 | 100 | White solid | 173-176 |
| 25 | 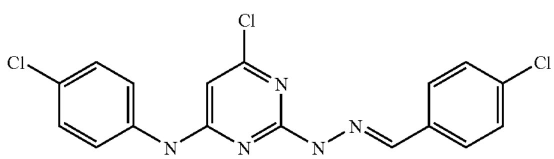 | 100 | 75 | Off-white solid | 234-236 |
| 26 | 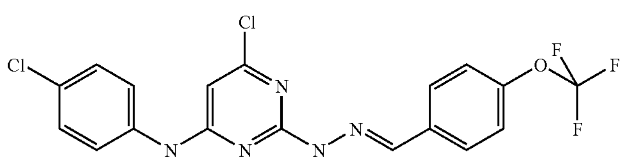 | 100 | 100 | White solid | 143-146 |
| 27 | 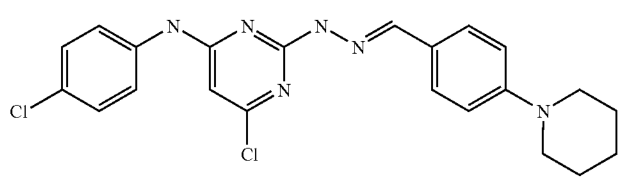 | 100 | 38 | yellow foam | 73-75 |
| 28 | 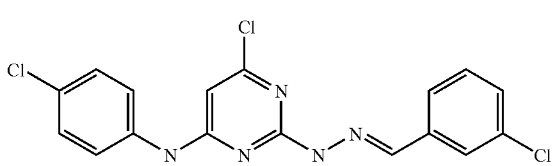 | 50 | 50 | White solid | 185-187 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 29 | 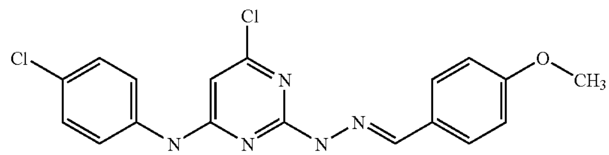 | 0 | 63 | Off-white solid | 171-173 |
| 30 | 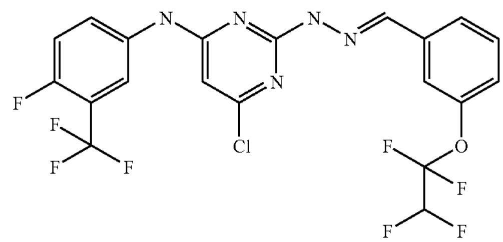 | 13 | 100 | light yellow solid | 172-174 |
| 31 | 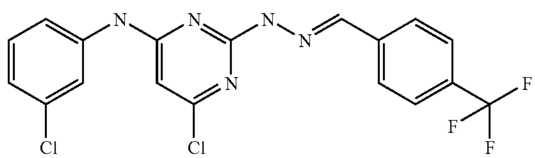 | 100 | 100 | light yellow solid | 165-167 |
| 32 | 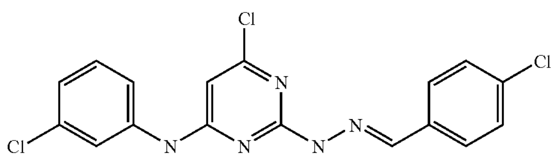 | 88 | 0 | Off-white solid | 219-220 |
| 33 | 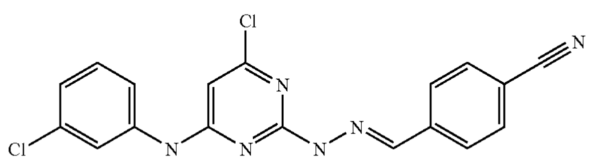 | 13 | 13 | Yellow solid | 289-290 |
| 34 | 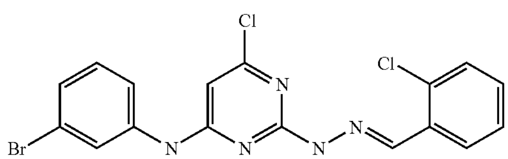 | 13 | 25 | Yellow solid | 189-190 |
| 35 | 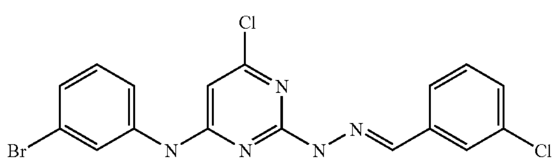 | 25 | 0 | White solid | 173-174 |
| 36 | 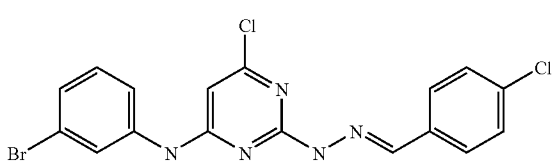 | 38 | 0 | White solid | 223-224 |
| 37 | 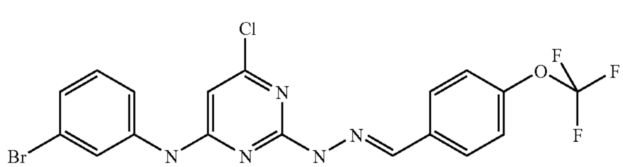 | 100 | 100 | White solid | 102-104 |

TABLE 1-continued
| Cpd # | Structure | HELIZE 50 (ug/cm2) | LAPHEG 50 (ug/cm2) | Phy. App. | mp (° C.) |
|---|---|---|---|---|---|
| 38 | 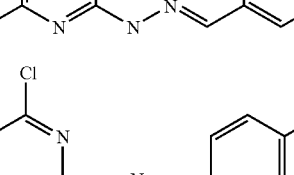 | 0 | 25 | Mauve solid | 178-180 |
| 39 | 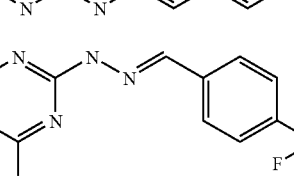 | 100 | 100 | Off-white solid | 148-150 |
| 40 | 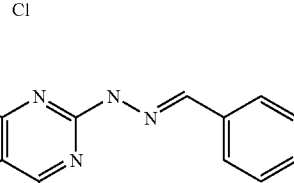 | 100 | 100 | white solid | 179-182 |
| 41 | 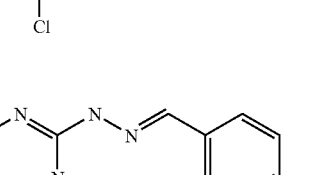 | 75 | 0 | white solid | 176-177 |
| 42 | 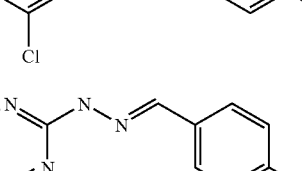 | 38 | 38 | white solid | 174-175 |
| 43 | 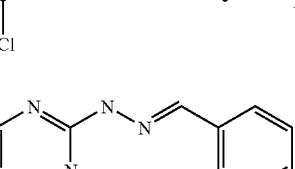 | 63 | 0 | light red foam | 115-120 |
| 44 | 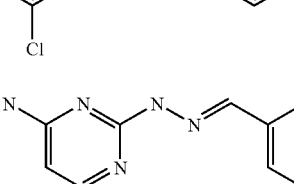 | 50 | 0 | green solid | 109-114 |
| 45 | 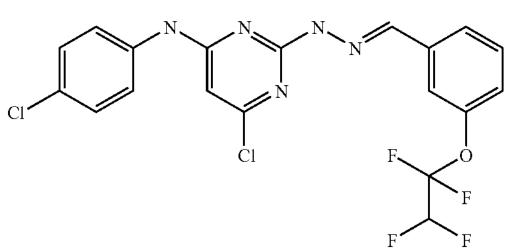 | 63 | 63 | white foam | 72-75 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 46 | 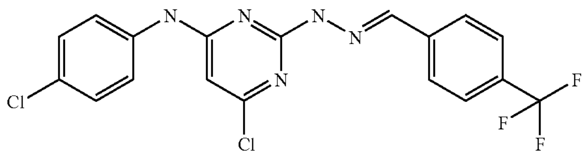 | 100 | 100 | white powder | 214-217 |
| 47 | 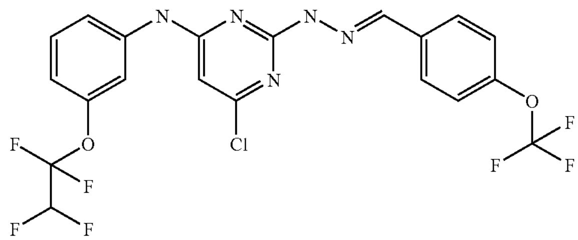 | 100 | 100 | light tan foam | 72-75 |
| 48 | 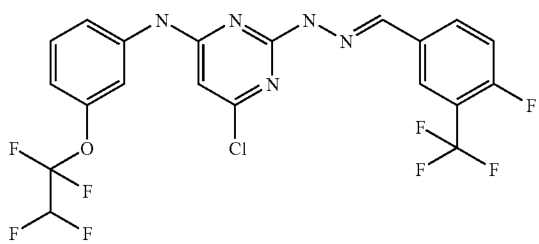 | 88 | 25 | tan solid | 136-139 |
| 49 | 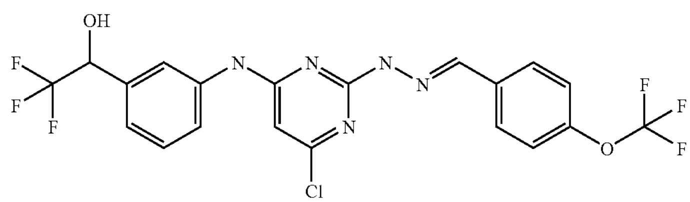 | 50 | 88 | white solid | 78-95 (amorphous solid) |
| 50 | 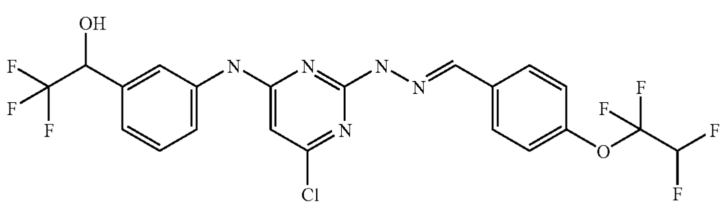 | 0 | 63 | white solid | 68-82 (amorphous solid |
| 51 | 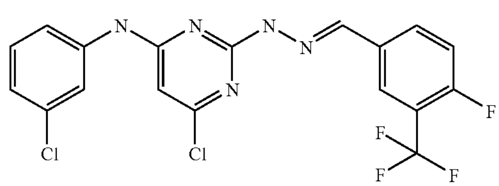 | 50 | 75 | off-white powder | 138-141 |
| 52 | 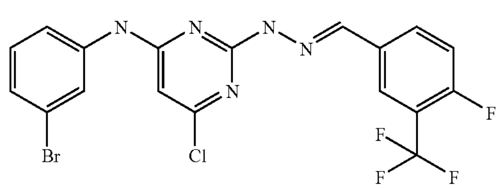 | 75 | 38 | off white powder | 183-185 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 53 | 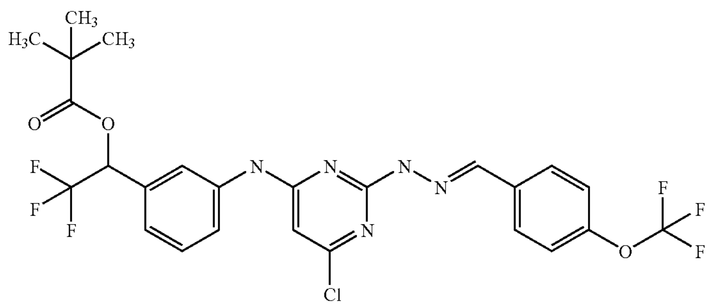 | 0 | 38 | white foam | 89-91 |
| 54 | 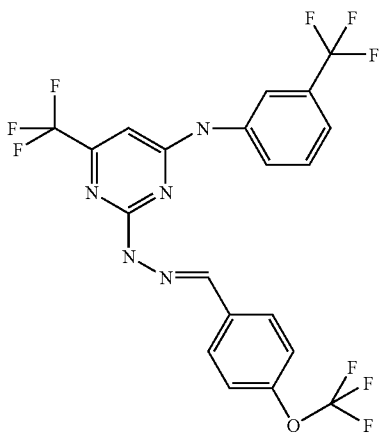 | 100 | 100 | white solid | 77-80 |
| 55 | 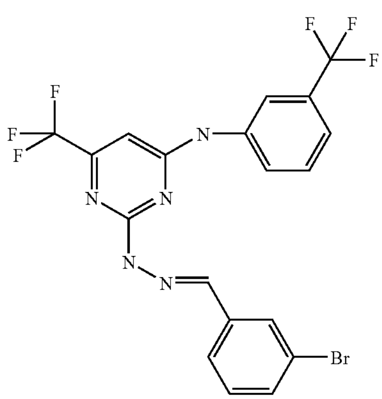 | 88 | 75 | white solid | 188-189 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 56 | 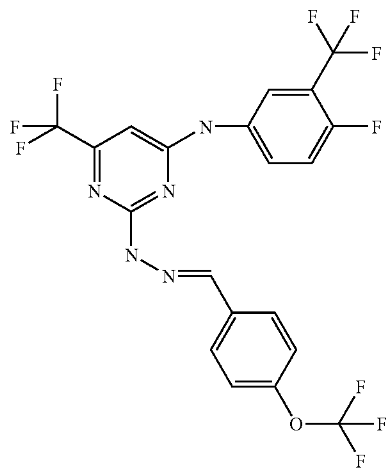 | 100 | 100 | light yellow solid | 112-115 |
| 57 | 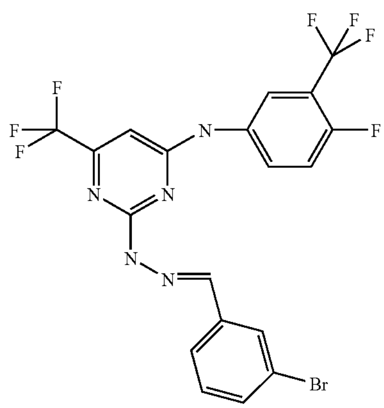 | 100 | 100 | light yellow solid | 198-200 |
| 58 | 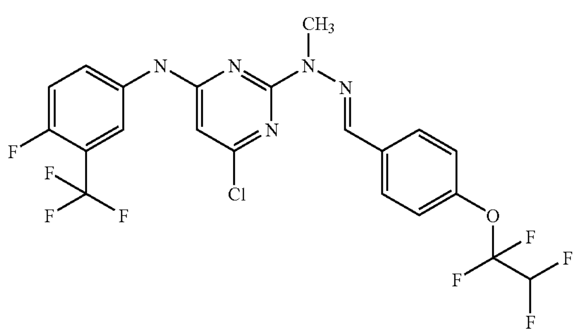 | 100 | 100 | light yellow solid | 80-85 |
| 59 | 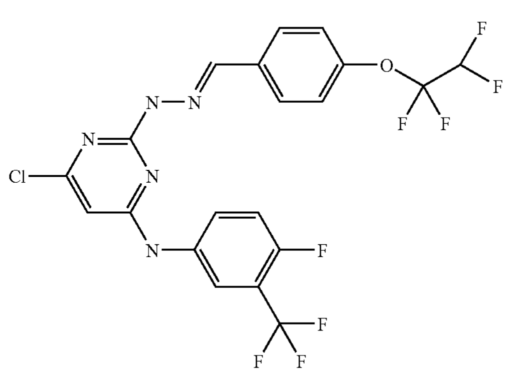 | 100 | 100 | white solid | 140-141 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 60 | 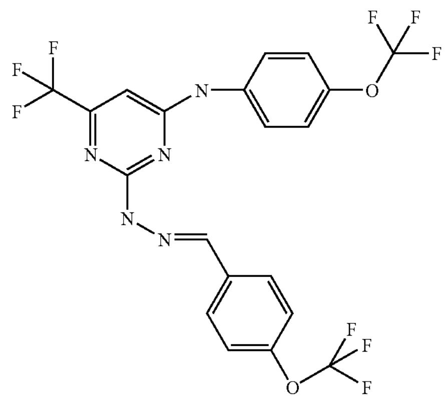 | 100 | 100 | yellow solid | 78-80 |
| 61 | 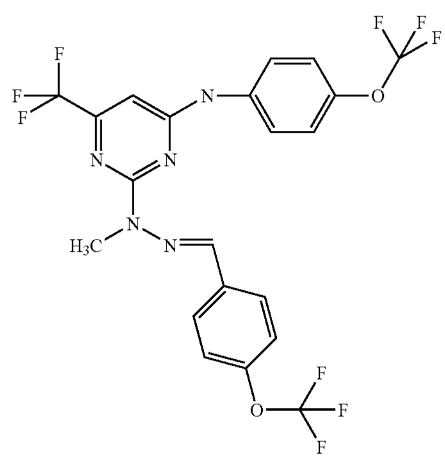 | 88 | 88 | yellow solid | 110-112 |
| 62 | 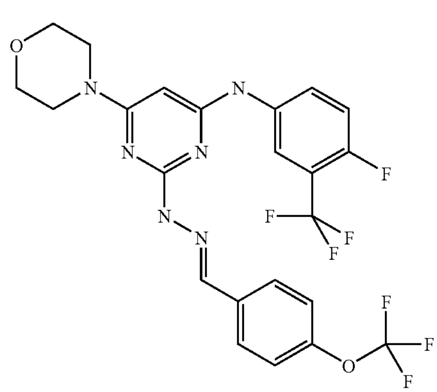 | 100 | 100 | white solid | 195-197 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 63 | 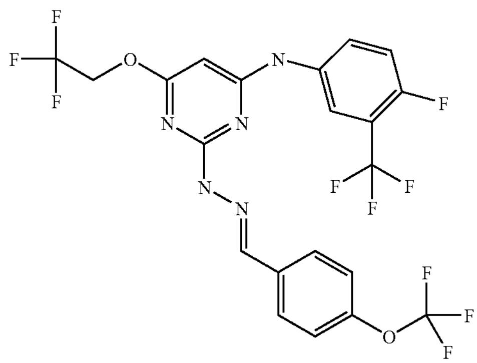 | 100 | 100 | white solid | 70-75 |
| 64 | 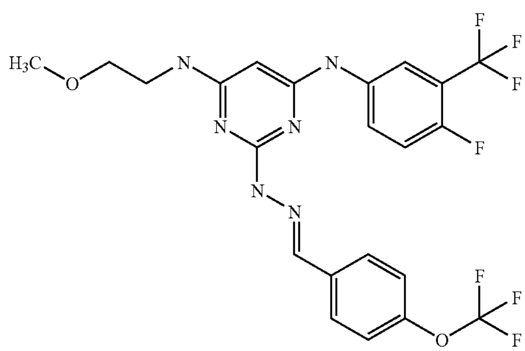 | 100 | 100 | off white solid | 90-95 |
| 65 | 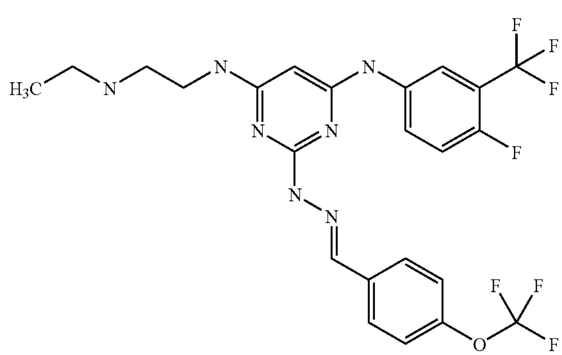 | 100 | 100 | off white solid | 110-125 |
| 66 | 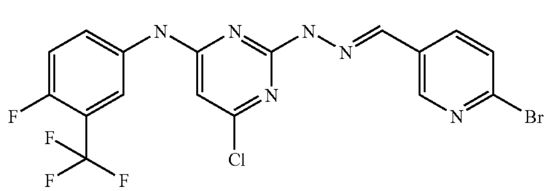 | 75 | 100 | white solid | 235-237 |
| 67 | 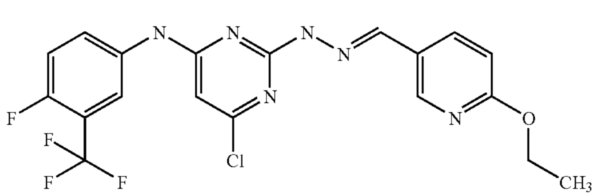 | 100 | 100 | yellow foam | 92-98 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 68 | 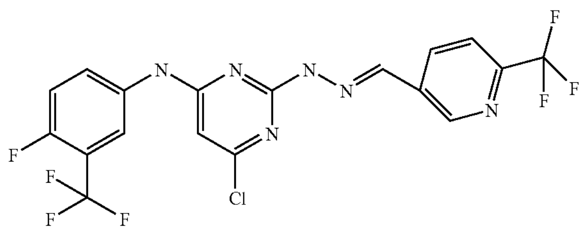 | 100 | 100 | light yellow solid | 200-204 |
| 69 | 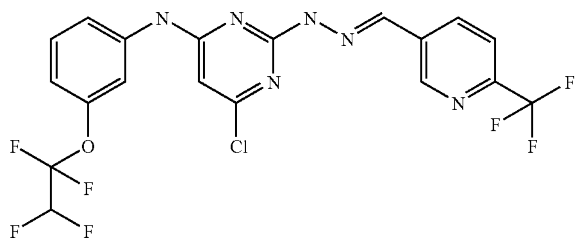 | 0 | 75 | light pink powder | 189-191 |
| 70 | 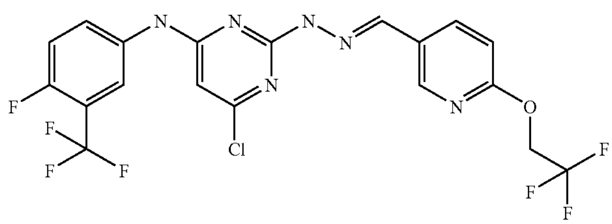 | 100 | 100 | off white solid | 183-185 |
| 71 | 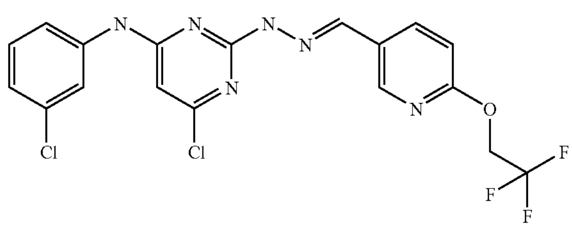 | 100 | 100 | off white powder | 120-125 |
| 72 | 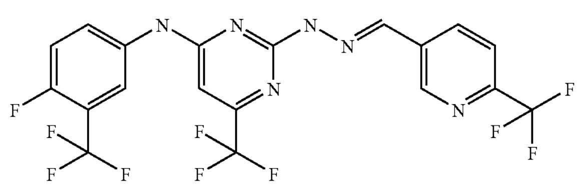 | 100 | 100 | light yellow solid | 184-187 |
| 73 | 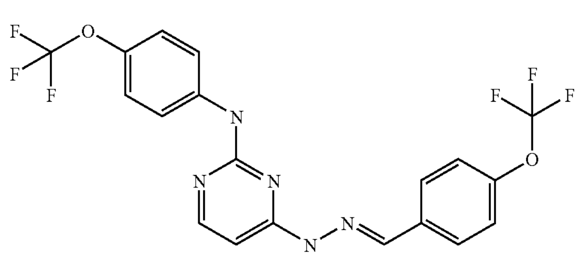 | 100 | 100 | tan solid | 190-202 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 74 | 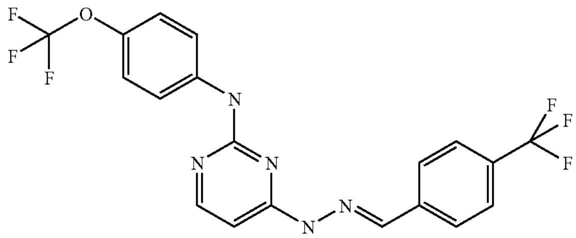 | 100 | 100 | orange waxy solid | n/a |
| 75 | 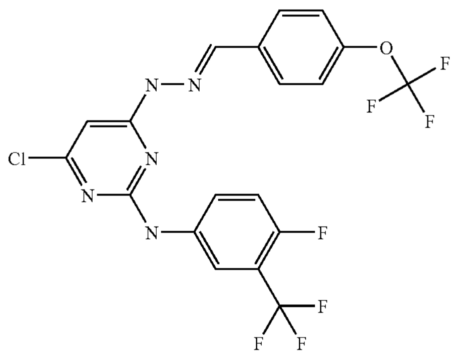 | 100 | 100 | white solid | 148-149 |
| 76 | 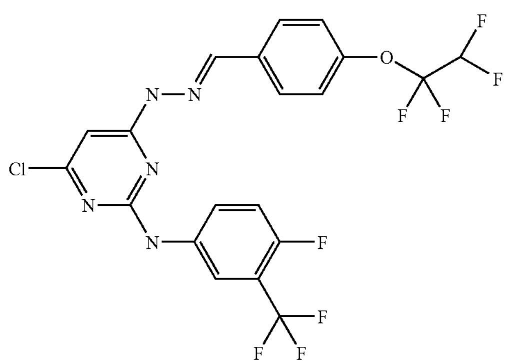 | 25 | 38 | white solid | 161-162 |
| 77 | 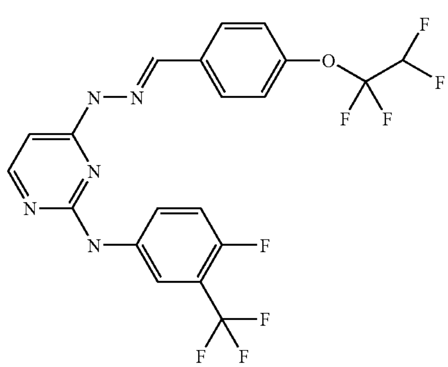 | 100 | 100 | white solid | 170-171 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 78 | 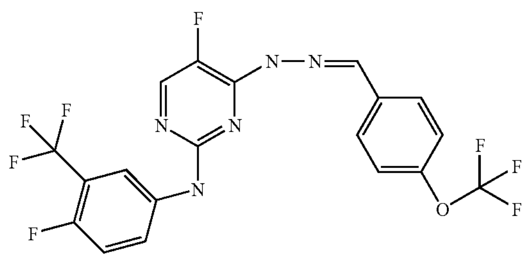 | 100 | 100 | tan solid | 167-169(d) |
| 79 | 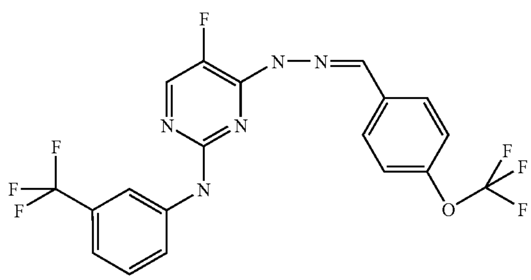 | 100 | 100 | tan solid | 173-175 |
| 80 | 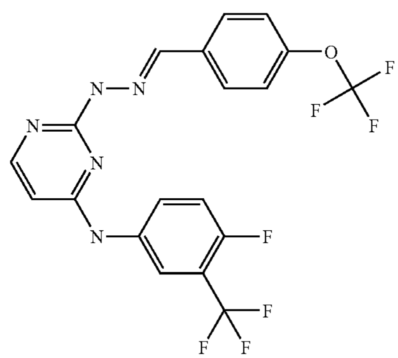 | 100 | 100 | white solid | n/a |
| 81 | 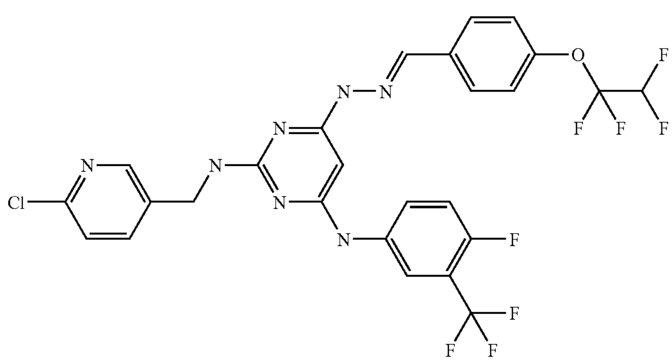 | 100 | 0 | white solid | 116-117 |
| 82 | 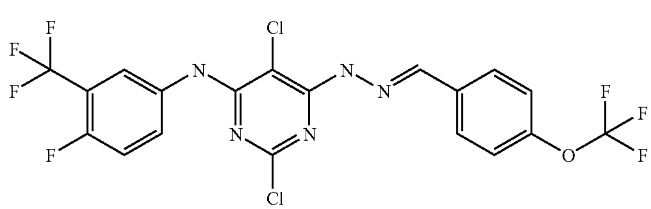 | 100 | 100 | brown solid | 210-211 |

TABLE 1-continued

| Cpd # | Structure | HELIZE 50 (ug/cm2) | LAPHEG 50 (ug/cm2) | Phy. App. | mp (° C.) |
|---|---|---|---|---|---|
| 83 | 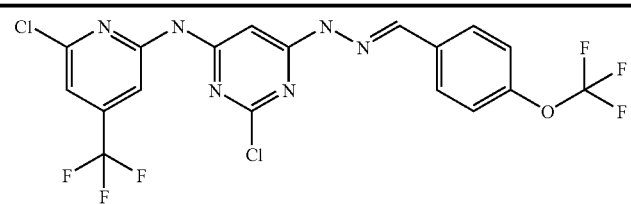 | 100 | 100 | white solid | 166-168 |
| 84 | 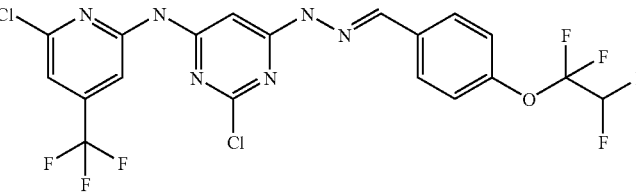 | 100 | 100 | white solid | 152-153 |
| 85 | 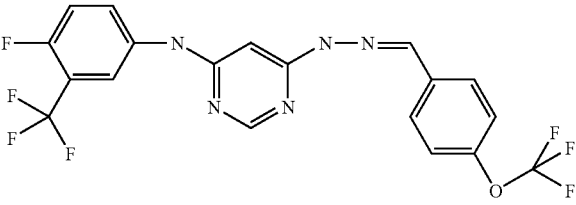 | 100 | 100 | light tan solid | 212-213 |
| 86 | 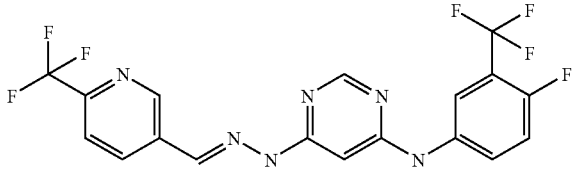 | 100 | 100 | light green solid | 224-229 |

Insecticide Utility

The compounds of the invention are useful for the control of invertebrates including insects. Therefore, the present invention also is directed to a method for inhibiting an insect which comprises applying an insect-inhibiting amount of a compound of formula (I) to a locus of the insect, to the area to be protected, or directly on the insect to be controlled. The compounds of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects or other pests which can be inhibited include, but are not limited to:

Lepidoptera—*Heliothis* spp., *Helicoverpa* spp., *Spodoptera* spp., *Mythimna unipuncta, Agrotis ipsilon, Earias* spp., *Euxoa auxiliaris, Trichoplusia ni, Anticarsia gemmatalis, Rachiplusia nu, Plutella xylostella, Chilo* spp., *Scirpophaga incertulas, Sesamia inferens, Cnaphalocrocis medinalis,*

*Ostrinia nubilalis, Cydia pomonella, Carposina niponensis, Adoxophyes orana, Archips argyrospilus, Pandemis heparana, Epinotia aporema, Eupoecilia ambiguella, Lobesia botrana, Polychrosis viteana, Pectinophora gossypiella, Pieris rapae, Phyllonorycter* spp., *Leucoptera malifoliella, Phyllocnisitis citrella*

Coleoptera—*Diabrotica* spp., *Leptinotarsa decemlineata, Oulema oryzae, Anthonomus grandis, Lissorhoptrus oryzophilus, Agriotes* spp., *Melanotus communis, Popillia japonica, Cyclocephala* spp., *Tribolium* spp.

Homoptera—*Aphis* spp., *Myzus persicae, Rhopalosiphum* spp., *Dysaphis plantaginea, Toxoptera* spp., *Macrosiphum euphorbiae, Aulacorthum solani, Sitobion avenae, Metopolophium dirhodum, Schizaphis graminum, Brachycolus noxius, Nephotettix* spp., *Nilaparvata lugens, Sogatella furcifera, Laodelphax striatellus, Bemisia tabaci, Trialeurodes vaporariorum, Aleurodes proletella, Aleurothrixus floccosus, Quadraspidiotus perniciosus, Unaspis yanonensis, Ceroplastes rubens, Aonidiella aurantii*

Hemiptera—*Lygus* spp., *Eurygaster maura, Nezara viridula, Piezodorus guildingi, Leptocorisa varicornis, Cimex lectularius, Cimex hemipterus*

Thysanoptera—*Frankliniella* spp., *Thrips* spp., *Scirtothrips dorsalis*

Isoptera—*Reticulitermes flavipes, Coptotermes formosanus, Reticulitermes virginicus, Heterotermes aureus, Reticulitermes hesperus, Coptotermes frenchii, Shedorhinotermes* spp., *Reticulitermes santonensis, Reticulitermes grassei, Reticulitermes banyulensis, Reticulitermes speratus, Reticulitermes hageni, Reticulitermes tibialis, Zootermopsis* spp., *Incisitermes* spp., *Marginitermes* spp., *Macrotermes* spp., *Microcerotermes* spp., *Microtermes* spp.

Diptera—*Liriomyza* spp., *Musca domestica, Aedes* spp., *Culex* spp., *Anopheles* spp., *Fannia* spp., *Stomoxys* spp., Hymenoptera—*Iridomyrmex humilis, Solenopsis* spp., *Monomorium pharaonis, Atta* spp., *Pogonomyrmex* spp., *Camponotus* spp., *Monomorium* spp., *Tapinoma sessile, Tetramorium* spp., *Xylocapa* spp., *Vespula* spp., *Polistes* spp.

Mallophaga (chewing lice)

Anoplura (sucking lice)—*Pthirus pubis, Pediculus* spp.

Orthoptera (grasshoppers, crickets)—*Melanoplus* spp., *Locusta migratoria, Schistocerca gregaria, Gryllotalpidae* (mole crickets).

Blattoidea (cockroaches)—B*latta orientalis, Blattella germanica, Periplaneta americana, Supella longipalpa, Periplaneta australasiae, Periplaneta brunnea, Parcoblatta pennsylvanica, Periplaneta fuliginosa, Pycnoscelusi surinamensis,*

Siphonaptera—*Ctenophalides* spp., *Pulex irritans*

Acari—*Tetranychus* spp., *Panonychus* spp., *Eotetranychus carpini, Phyllocoptruta oleivora, Aculus pelekassi, Brevipalpus phoenicis, Boophilus* spp., *Dermacentor variabilis, Rhipicephalus sanguineus, Amblyomma americanum, Ixodes* spp., *Notoedres cati, Sarcoptes scabiei, Dermatophagoides* spp.

Nematoda—*Dirofilaria immitis, Meloidogyne* spp., *Heterodera* spp., *Hoplolaimus columbus, Belonolaimus* spp., *Pratylenchus* spp., *Rotylenchus reniformis, Criconemella ornata, Ditylenchus* spp., *Aphelenchoides besseyi, Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and/or nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsulated insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae, B. sphaericus, B. thuringiensis* subsp. *aizawai, B. thuringiensis* subsp. *kurstaki, B. thuringiensis* subsp. *tenebrionis, Beauveria bassiana, Cydia pomonella* granulosis virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A.105, Cry2Ab2, Cry3A, mir Cry3A, Cry3B1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, Candida oleophila, Fusarium oxysporum, Gliocladium spp., Phlebiopsis gigantean, Streptomyces griseoviridis, Trichoderma spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

We claim:

1. A compound of formula (I)

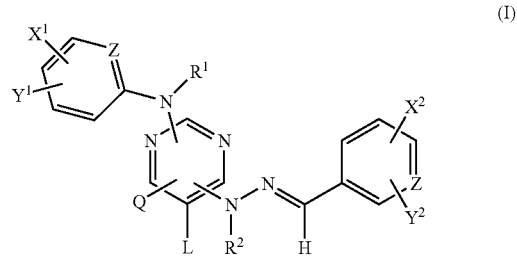

wherein $X^1$ and $Y^1$ independently represent H, halogen, $C_1$-$C_6$ haloalkyl, $C_1$-$C_6$ haloalkoxy, $C_1$-$C_6$ halothioalkyl, or $C_1$-$C_6$ haloalkyl substituted with hydroxy or $C_1$-$C_6$ acyloxy, with the proviso that at least one of $X^1$ or $Y^1$ is not H;

$X^2$ and $Y^2$ independently represent H, halogen, CN, $C_1$-$C_6$ alkoxy, $C_1$-$C_6$ haloalkyl, $C_1$-$C_6$ haloalkoxy, $C_1$-$C_6$ halothioalkyl, 1-pyrrolidinyl, 1-piperidinyl, or $C_1$-$C_6$ haloalkyl substituted with a substituent selected from the group consisting of hydroxy and $C_1$-$C_6$ acyloxy, with the proviso that at least one of $X^2$ or $Y^2$ is not H;

Z represents CH or N;

L represents H, halogen or $C_1$-$C_3$ haloalkyl;

Q represents H, halogen, $OR^3$, $C_1$-$C_3$-haloalkyl, $SR^5$ or $NR^4R^5$;

$R^1$ and $R^2$ independently represents H or $CH_3$;

$R^3$ represents $C_1$-$C_4$ alkyl which may be unsubstituted or substituted with from one to the maximum number of chloro or fluoro substituents;

$R^4$ represents H or $C_1$-$C_4$ alkyl; and $R^5$ represents
- $C_1$-$C_4$ alkyl, which may be unsubstituted, or substituted with from one to the maximum number of chloro or fluoro substituents, or with a substituent selected from the group consisting of $C_1$-$C_4$ alkoxy, $C_1$-$C_4$ alkylamino, and a pyridin-3-yl substituted in the 6-position of the pyridine ring with halogen,
- $C_1$-$C_4$ alkoxy, or
- $C_1$-$C_4$ haloalkyl.

2. A compound according to claim 1 in which Z is CH.

3. A compound according to claim 1 in which one of $X^1$ and $Y^1$ is F, Cl, Br, CN, $CF_3$, $OCF_3$, $OCF_2CHF_2$ or $CH(CF_3)OH$.

4. A compound according to claim 3 in which $X^1$ and $Y^1$ are meta- or para-substituents relative to the —$NR^1$— substituent.

5. A compound according to claim 1 in which one of $X^2$ and $Y^2$ is F, Cl, Br, CN, $CF_3$, $OCF_3$, 1-pyrollidinyl, 1-piperidinyl, $OCF_2CHF_2$ or $C(CF_3)_2OH$.

6. A compound according to claim 5 in which $X^2$ and $Y^2$ are meta- or para-substituents relative to the —CH=N—N—$R^2$— substituent.

7. A compound according to claim 1 in which Q is H, Cl, F, $CF_3$, $CH_3OCH_2CH_2NH$, $EtNHCH_2CH_2NH$, $CF_3CH_2O$, or

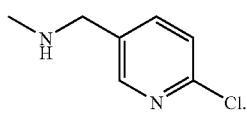

8. A compound according to claim 1 in which L is H, Cl, F or $CF_3$.

9. A compound according to claim 1 having the structure

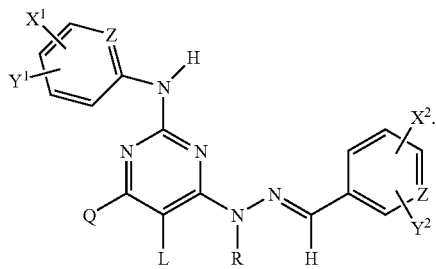

10. A compound according to claim 1 having the structure

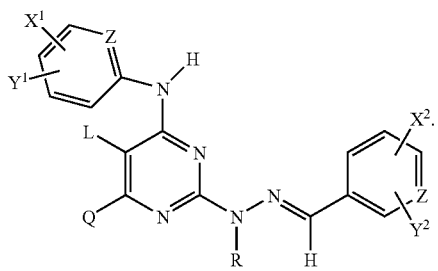

11. A compound according to claim 1 having the structure

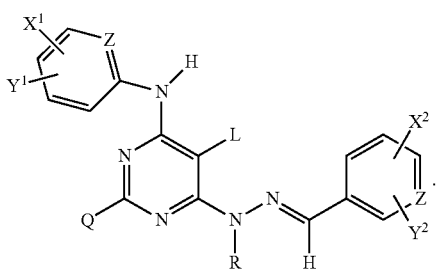

12. A composition for controlling insects which comprises a compound of claim 1 in combination with a phytologically-acceptable carrier.

13. A method of controlling insects which comprises applying to a locus where control is desired an insect-inactivating amount of a compound of claim 1.

14. A compound according to claim 1 having the following structure

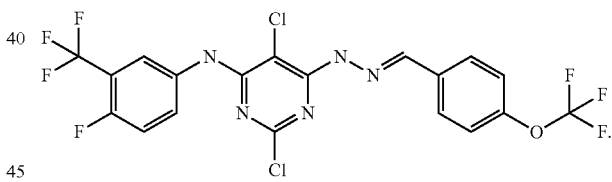

* * * * *